United States Patent
Talin et al.

(10) Patent No.: US 10,429,343 B1
(45) Date of Patent: Oct. 1, 2019

(54) TUNABLE IONIC ELECTRONIC TRANSISTOR

(71) Applicant: Sandia Corporation, Albuquerque, NM (US)

(72) Inventors: Albert Alec Talin, Dublin, CA (US); Farid El Gabaly Marquez, Berkeley, CA (US); Elliot James Fuller, Pleasanton, CA (US); Sapan Agarwal, Dublin, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 318 days.

(21) Appl. No.: 15/428,325

(22) Filed: Feb. 9, 2017

(51) Int. Cl.
*H01L 45/00* (2006.01)
*G01N 27/414* (2006.01)
*G01N 27/04* (2006.01)

(52) U.S. Cl.
CPC ......... *G01N 27/4148* (2013.01); *G01N 27/04* (2013.01); *H01L 45/1206* (2013.01); *H01L 45/1266* (2013.01); *H01L 45/145* (2013.01); *H01L 45/148* (2013.01)

(58) Field of Classification Search
CPC combination set(s) only.
See application file for complete search history.

(56) References Cited

U.S. PATENT DOCUMENTS

| | | | |
|---|---|---|---|
| 6,653,193 B2 | 11/2003 | Gilton | |
| 6,992,323 B2 | 1/2006 | Krieger et al. | |
| 8,035,175 B2 | 10/2011 | Shim et al. | |
| 8,946,785 B2 | 2/2015 | Lim et al. | |
| 9,230,985 B1* | 1/2016 | Wu | H01L 27/11582 |
| 10,083,974 B1* | 9/2018 | Huang | H01L 27/11521 |
| 2005/0156584 A1 | 7/2005 | Feng | |
| 2006/0022347 A1* | 2/2006 | Campbell | H01L 45/1641 257/762 |
| 2010/0327255 A1 | 12/2010 | Peng et al. | |
| 2013/0140531 A1* | 6/2013 | Park | H01L 51/0097 257/40 |

(Continued)

OTHER PUBLICATIONS

Greenlee, et al., "In Situ Investigation of the Channel Conductance of a Li1-xCoO2 (0<x<0.5) Ionic-Electronic Transistor", In Applied Physics Letters, 2013, vol. 102, 5 pages.

(Continued)

*Primary Examiner* — Seahvosh Nikmanesh
(74) *Attorney, Agent, or Firm* — Gregory M. Doudnikoff

(57) ABSTRACT

Various technologies pertaining to a transistor having a variable-conductance channel with a non-volatile tunable conductance are described herein. The transistor comprises source and drain electrodes separated by a conducting channel layer. The conducting channel layer is separated from an electrochemical gate (ECG) layer by an electrolyte layer that prevents migration of electrons between the channel and the ECG but allows ion migration. When a voltage is applied between the channel and the ECG, electrons flow from one to the other, which causes a migration of ions from the channel to the ECG or vice versa. As ions move into or out of the channel layer, the conductance of the channel changes. When the voltage is removed, the channel maintains its conductance state.

10 Claims, 4 Drawing Sheets

(56) References Cited

U.S. PATENT DOCUMENTS

| | | | |
|---|---|---|---|
| 2014/0150859 A1* | 6/2014 | Zakhidov | H01L 51/445 136/255 |
| 2015/0070966 A1* | 3/2015 | Bandyopadhyay | G11C 13/0069 365/148 |
| 2015/0325278 A1* | 11/2015 | Bauer | H01L 43/08 365/158 |
| 2016/0363559 A1 | 12/2016 | Rudzevich et al. | |
| 2019/0131555 A1* | 5/2019 | Doris | H01L 51/0508 |
| 2019/0164834 A1* | 5/2019 | Or-Bach | H01L 21/8221 |

OTHER PUBLICATIONS

Shi, et al., "A Correlated Nickelate Synaptic Transistor", In Nature Communications, Oct. 21, 2013, 9 pages.

Mai, et al., "Memristive and Neuromorphic Behavior in a $Li_xCoO_2$ Nanobattery", In Scientific Reports, Jan. 14, 2015, 6 pages.

Moradpour et al., "Resistive Switching Phenomena in $Li_xCoO_2$ Thin Films", In Advanced Materials, 2011, pp. 1141-4145, vol. 23.

\* cited by examiner

TUNABLE IONIC ELECTRONIC TRANSISTOR

STATEMENT OF GOVERNMENTAL INTEREST

This invention was developed under Contract DE-AC04-94AL85000 between Sandia Corporation and the U.S. Department of Energy. The U.S. Government has certain rights in this invention.

BACKGROUND

Complementary metal-oxide-semiconductor (CMOS) transistors are nearly ubiquitous in their implementation in various electronic devices. As continued downscaling of CMOS devices has become more difficult, other computing devices and technologies have emerged. Resistive memory (memristor) devices have been developed that comprise arrays of two terminal resistors with at least partially programmable resistance. Memristor devices have included memristor units built using transition metal oxides, phase change materials, or polymers sandwiched between metallic electrodes. These memristor units generally exhibit non-idealities that limit their applications: 1) read noise that causes a value read from the memristor device to be different from a true value, 2) write noise that causes a value written to the memristor device to be different from an intended value, and 3) write non-linearity, which causes a change in conductance resulting from a given write pulse to change depending on the current conductance state of the device. Three-terminal devices exhibiting memristor-like functions have been developed that use an ionic liquid gate to control a source-to-drain resistance via injection or extraction of oxygen vacancies in the liquid. These liquid gate devices are difficult to integrate with solid-state devices (e.g., CMOS-based devices), however, and have slow switching speeds (on the order of seconds).

SUMMARY

The following is a brief summary of subject matter that is described in greater detail herein. This summary is not intended to be limiting as to the scope of the claims.

Various technologies pertaining to an ionic electronic transistor are described herein. In an exemplary embodiment, an ionic electronic transistor comprises source and drain electrodes and a conduction channel that separates the source and the drain. Responsive to application of a voltage between the source and the drain, and depending on a polarity and magnitude of the voltage applied, electrons flow either from the source to the drain or from the drain to the source by way of the conduction channel. In an example, the conduction channel can be a layer of deposited material that is deposited on top of the source and drain electrodes such that the electrodes are separated by the conduction channel material.

The conduction channel comprises a material with a conductivity that can be changed responsive to migration of ions into or out of the channel. The ionic transistor can further comprise an electrolyte layer and an electrochemical gate layer. The electrolyte layer is positioned such that a first side of the electrolyte layer makes contact with a side of the conduction channel and the electrochemical gate layer is deposited on a second opposite side of the electrolyte layer. The electrochemical gate layer comprises a material that can accept ions from or provide ions to the conducting channel layer. The electrolyte comprises a material that prevents migration of ions between the electrochemical gate layer and the conducting channel layer absent a voltage being applied between the electrochemical gate layer and the conducting channel layer, but that allows ions to migrate between those layers responsive to such a voltage being applied. When a voltage is applied between the electrochemical gate layer and the channel layer, an electrical current flows. As electrons flow, ions move through the electrolyte layer from the channel to the electrochemical gate or vice versa depending upon a polarity of the voltage. A number of ions that move from one layer to another is dependent upon a magnitude and duration of the voltage applied between the channel and the electrochemical gate. Since conductivity of the channel layer is dependent upon the concentration of ions in the channel, as ions migrate and thereby increase or decrease their concentration, the conductivity changes. The change in conductivity is directly dependent upon the concentration of ions in the channel, and thus the conductivity of the channel can be predictably tuned based upon application of voltage pulses of defined magnitude and duration between the electrochemical gate and the channel.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
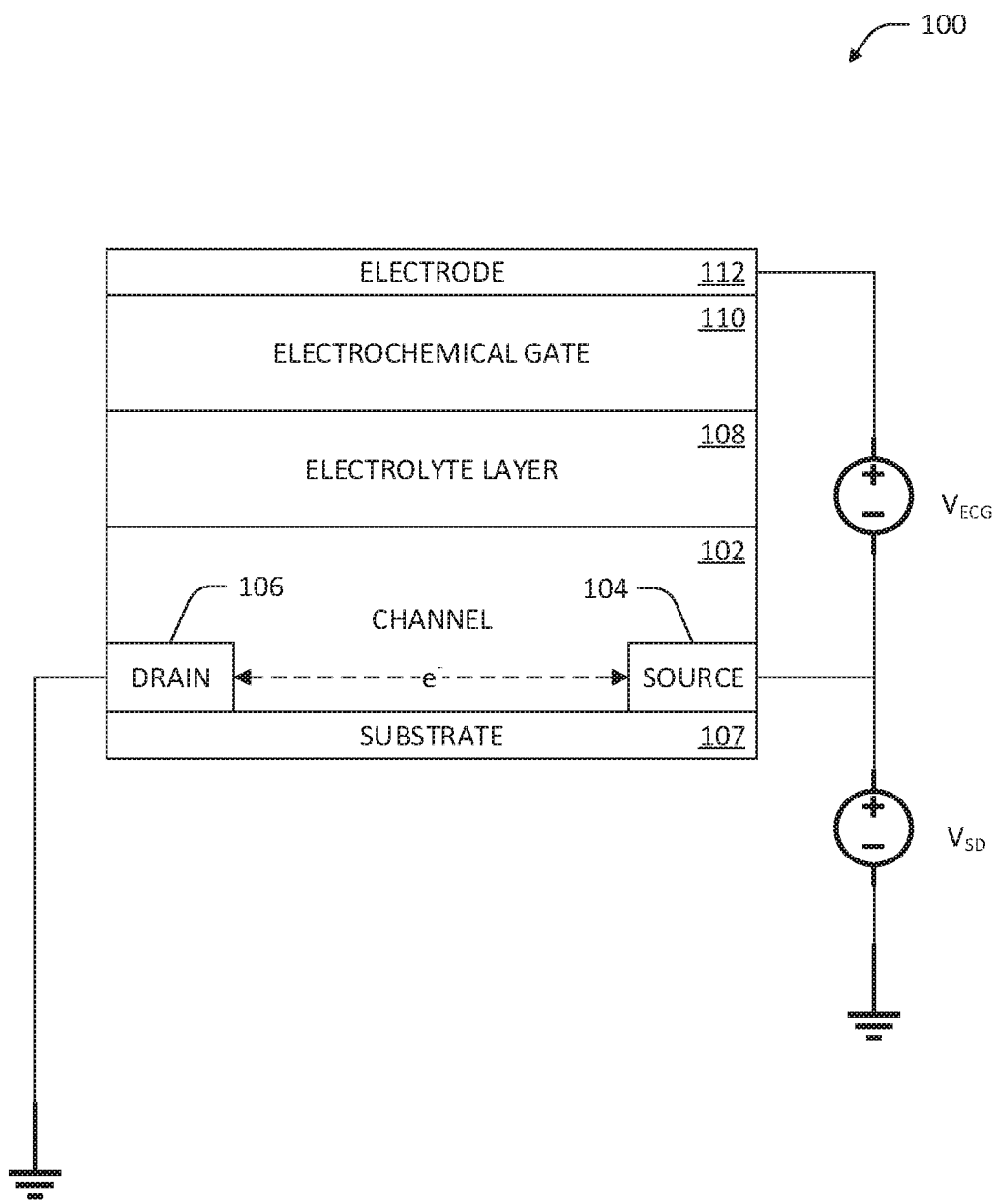
FIG. 1 is a block diagram of an exemplary ionic transistor.

Various technologies pertaining to a tunable ionic electronic transistor are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

With reference to FIG. 1, an exemplary transistor 100 is illustrated. The transistor 100 includes a channel layer of variable conductivity 102, a source electrode 104 and a drain electrode 106. The source electrode 104 and the drain electrode 106 are separated from one another by the channel 102 such that the source 104 and the drain 106 do not make physical contact. By way of example, the source 104 and drain 106 electrodes can be deposited at some distance apart from one another (e.g., tens of nanometers) on a substrate layer 107 comprising a material such as silicon dioxide ($SiO_2$), and the channel layer 102 can be deposited on top of and between the source 104 and the drain 106. The transistor 100 further comprises an electrolyte layer 108 that separates the channel from an electrochemical gate (ECG) layer 110. Continuing the example, the electrolyte layer 108 can be deposited on a top side of the channel layer 102 opposite a bottom side of the channel layer 102 that is in contact with the source 104 and the drain 106. The ECG layer 110 can be deposited on a top side of the electrolyte layer 108, the top side of the electrolyte layer 108 opposite a bottom side of the electrolyte layer 108 that makes contact with the top side of the channel layer 102. Accordingly, in an exemplary embodiment the source 104 and drain 106 are deposited on top of the substrate 107, the channel layer 102 is deposited between and on top of the source 104 and the drain 106, the electrolyte layer 108 is deposited on top of the channel layer 102, and the ECG layer 110 can be deposited on top of the electrolyte layer 108. In such exemplary embodiment, the transistor 100 can be fabricated by techniques such as photolithography.

The channel 102 of the transistor 100 comprises a material that has a conductivity that depends on its oxidation level. Thus, the conductivity of the channel 102 can be changed by oxidation or reduction of the channel 102. Exemplary materials for the channel 102 having a conductivity that varies based on oxidation level include inorganic materials. These inorganic materials can include lithium compounds such as $Li_xCoO_2$, $Li_xNiO_2$, $Li_xMn_2O_4$, $Li_xV_2O_5$, $Li_xWO_3$, $Li_xMO_3$, $Li_xTi_5O_{12}$, etc., where x represents a variable fraction of lithium present in a compound. Other exemplary materials for the channel 102 include alloys of inorganic materials. Other inorganic materials include sodium compounds such as $NaWO_3$. Still other exemplary materials for the channel 102 include organic polymers such as poly(3,4-ethylenedioxythiophene) (PEDOT), PEDOT:Polystyrene sulfonate (PEDOT:PSS), PEDOT:PSS partially reduced with Poly(ethylenimine) (PEI), and polyaniline. Oxidation or reduction of the channel 102 occurs as the result of electron flow between the channel 102 and the ECG 110 caused by application of the voltage $V_{ECG}$, which electron flow itself causes migration of ions between the channel 102 and the ECG 110 through the electrolyte layer 108. The electrolyte layer 108 comprises a material that allows fast transport of ions between the ECG 110 and the channel 102, but blocks transport of electrons. The ECG 110 comprises a material that can accept ions from the channel layer 102.

Oxidation or reduction of the channel 102 can be controlled by application of a voltage between the ECG 110 and the channel 102. The voltage can be applied by way of an electrode 112 deposited on top of the ECG layer 110 and the source electrode 104, as shown in FIG. 1 as $V_{ECG}$. In an example, responsive to application of a positive $V_{ECG}$, where positive refers to a drop in electrical potential from the ECG 110 to the source 104, electrons flow from the ECG 110 to the channel 102 by way of the source electrode 104, while positively charged ions are transported from the ECG to the channel through the electrolyte layer 108. In oxidation of the channel 102, electrons are transferred from the channel 102 to the ECG 110 through the source electrode 104 while positive ions are transported from the channel 102 to the ECG 110 through the electrolyte layer 108. In reduction of the channel 102, electrons are transferred from the ECG 110 to the channel 102 through the source electrode 104 while positive ions are transported from the ECG 110 to the channel 102 through the electrolyte layer 108.

The conductance of the channel 102 can be reversibly changed in a linear fashion responsive to voltage pulses applied between the ECG 110 and the channel 102 (or metallic electrodes in contact with the ECG 110 and the channel 102, such as the electrodes 112 and 104, respectively). A change in conductance of the channel 102 exhibits a linear dependence on a number of ions that migrate into or out of the channel 102. A number of ions that migrate into or out of the channel 102 responsive to a voltage pulse applied at $V_{ECG}$ depends upon a magnitude and duration of the voltage pulse, but also exhibits a linear relationship. Thus, two voltage pulses of equal magnitude and duration cause a same change in conductance of the channel 102. Furthermore, pulses of equal duration and equal but opposite magnitude cause equal but opposite changes in the conductance of the channel 102.

Figure 2:
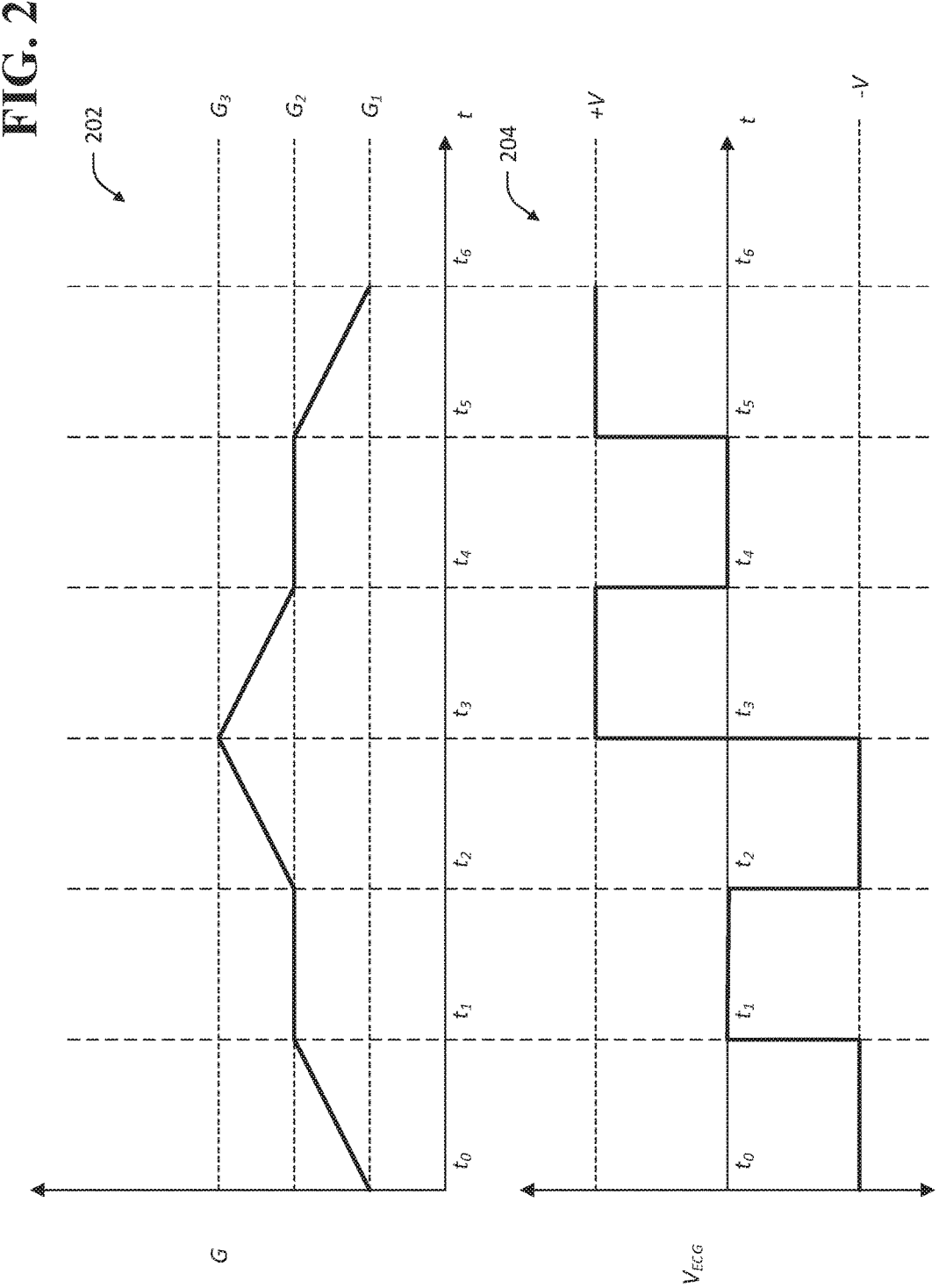
FIG. 2 illustrates exemplary channel conductance and electrochemical gate voltage plots.

To illustrate further, and referring now to FIG. 2, an exemplary channel conductance plot 202 and an exemplary ECG voltage plot 204 are illustrated. From time $t_0$ to time $t_1$, the voltage $V_{ECG}$ takes the value $-V$, such that there is a drop in electric potential from the channel 102 to the ECG 110. As a result, in the same period, the conductance of the channel 102, G, undergoes a substantially linear increase from $G_1$ to $G_2$ as ions migrate into or out of the channel 102, which direction of migration may depend upon whether the ions are positive or negative, a material-dependent factor. From $t_1$ to $t_2$, $V_{ECG}$ is zero, and the conductance G does not change. Once an oxidation level of the channel 102 is set by way of application of a voltage pulse between the source 104 and the electrode 112 that is deposited on the ECG 110, the conductance of the channel 102 remains stable until another voltage pulse is applied between the source 104 and the electrode 112. Thus, when no voltage is applied, the conductance of the channel 102 stays constant. From $t_2$ to $t_3$ the voltage $V_{ECG}$ takes the value $-V$ again, and the conductance G undergoes another substantially linear increase from $G_2$ to $G_3$. Since the same voltage is applied for the same duration, the conductance increase from $G_2$ to $G_3$ is substantially the same magnitude as the conductance increase from $G_1$ to $G_2$ (e.g., ±5%). From $t_3$ to $t_4$, the voltage $V_{ECG}$ takes the value $+V$, equal and opposite to the magnitude of the voltage $V_{ECG}$ from time $t_2$ to $t_3$. In the same period $t_3$ to $t_4$, the conductance G undergoes a substantially linear decrease from $G_3$ to $G_2$. Thus, two voltage pulses at $V_{ECG}$ of the same duration and equal but opposite magnitudes yield conductance changes that cancel one another. In the period $t_4$ to $t_5$, the conductance G does not change since there is no $V_{ECG}$ applied between the ECG 110 and the channel 102. From $t_5$ to $t_6$, the voltage $V_{ECG}$ takes the value $+V$, and thus the conductance G decreases from $G_2$ to $G_1$.

The time to change the resistance or conductance state of the channel 102 depends at least in part upon the thickness of the channel layer 102 (e.g., where the thickness refers to a separation distance of the channel 102 between the electrolyte layer 108 and the substrate 107). Thus, in some embodiments it may be desirable that the channel layer 102 is relatively thin (e.g., 1-100 nanometers) in order to improve a response time over which the conductance of the channel 102 changes in response to a voltage pulse $V_{ECG}$.

The time to change the resistance or conductance state of the channel 102 also depends at least in part upon the ionic conductance of the electrolyte layer 108. Thus, in some embodiments it may be desirable that the electrolyte layer 108 is relatively thin (e.g., 10-100 nanometers) in order to improve a response time over which the conductance of the channel 102 changes in response to a voltage pulse $V_{ECG}$.

The channel 102 of the transistor 100 can have a large number of different conductance states (e.g., 300-500 distinct states) responsive to a plurality of voltage pulses being applied at $V_{ECG}$. In one example, the channel 102 can take a plurality of 500 different conductance states in a range from approximately 525 μS to 825 μS responsive to a plurality of 500 voltage pulses of approximately 1.5 mV at $V_{ECG}$. In another example, the channel 102 can take a plurality of 35 different conductance states in a range from approximately 700 μS to 2250 μS responsive to a plurality of 35 voltage pulses of approximately 10 mV at $V_{ECG}$.

A first exemplary embodiment of the transistor 100 is now described wherein the channel 102 and the ECG 110 comprise nonorganic compounds. In the embodiment, the channel 102 comprises $LiCoO_2$, the electrolyte layer 108 comprises lithium phosphorous oxynitride (LiPON), and the ECG 110 comprises a material that can accept $Li^+$ ions from the $LiCoO_2$ channel 102 (e.g., Si, $LiCoO_2$, etc.). Responsive to a negative $V_{ECG}$ pulse being applied from the ECG electrode 112 to the source electrode 104, electrons and $Li^+$ ions flow from the $LiCoO_2$ channel 102 into the ECG 110. As Li ions leave the $LiCoO_2$ channel 102, the conductance of the channel 102 increases as the migration of the Li ions forms mobile hole polarons in the $LiCoO_2$ structure. Similarly, responsive to a positive $V_{ECG}$ pulse being applied from the ECG electrode 112 to the source electrode 104, electrons and $Li^+$ ions flow from the ECG 110 into the $LiCoO_2$ channel 102, and the conductance of the channel 102 decreases as the injected electrons reduce the mobile polaron concentration in the $LiCoO_2$. In the first exemplary embodiment of the transistor 100, the $LiCoO_2$ channel 102 can have a thickness of approximately 1-120 nm, the LiPON electrolyte layer 108 can have a thickness of approximately 20-400 nm, and the ECG 110 layer can have a thickness of approximately 10-50 nm. The source electrode 104, the drain electrode 106, and the ECG electrode 112 can comprise platinum or other high-conductivity metals. The source 104 and the drain 106 can be separated from one another by the channel 102 with a spacing of tens of nanometers to several micrometers. It is to be understood that other thicknesses, dimensions, and materials are contemplated.

A second exemplary embodiment of the transistor 100 is now described wherein the channel 102 and the ECG 110 comprise organic polymers. In the embodiment, the channel 102 comprises PEDOT:PSS partially reduced with PEI, the electrolyte layer 108 comprises a tetrafluoroethylene-based fluoropolymer-copolymer electrolyte (e.g., Nafion), and the ECG 110 comprises PEDOT:PSS. Responsive to a negative $V_{ECG}$ pulse being applied from the ECG electrode 112 to the source electrode 104, electrons and $H^+$ ions flow from the PEDOT:PSS/PEI channel 102 into the PEDOT:PSS ECG 110. As the $H^+$ ions leave the channel 102, conductance of the channel 102 increases. Similarly, in responsive to a positive $V_{ECG}$ pulse being applied from the ECG electrode 112 to the source electrode 104, electrons and $H^+$ ions flow from the ECG 110 into the PEDOT:PSS/PEI channel 102, and the conductance of the channel 102 decreases.

In other exemplary embodiments, the channel layer 102 and the ECG 110 comprise a same material. When the channel 102 and the ECG 110 are made from a same material, the transistor 100 can have an operating point of approximately 0 V between the channel layer 102 and the ECG 110. Programming of the transistor 100 is simplified when the voltage between the channel layer 102 and the ECG 110 is close to zero. Further, when the voltage between the channel layer 102 and the ECG 110 is small (e.g., less than or equal to 1.5 V) the electrolyte layer 108 can comprise a solid electrolyte, such as $Li_3N$, that may be unsuitable for higher voltages (e.g., greater than or equal to 3.5 V). Solid electrolytes can have a higher ionic conductivity than other materials.

Figure 3:
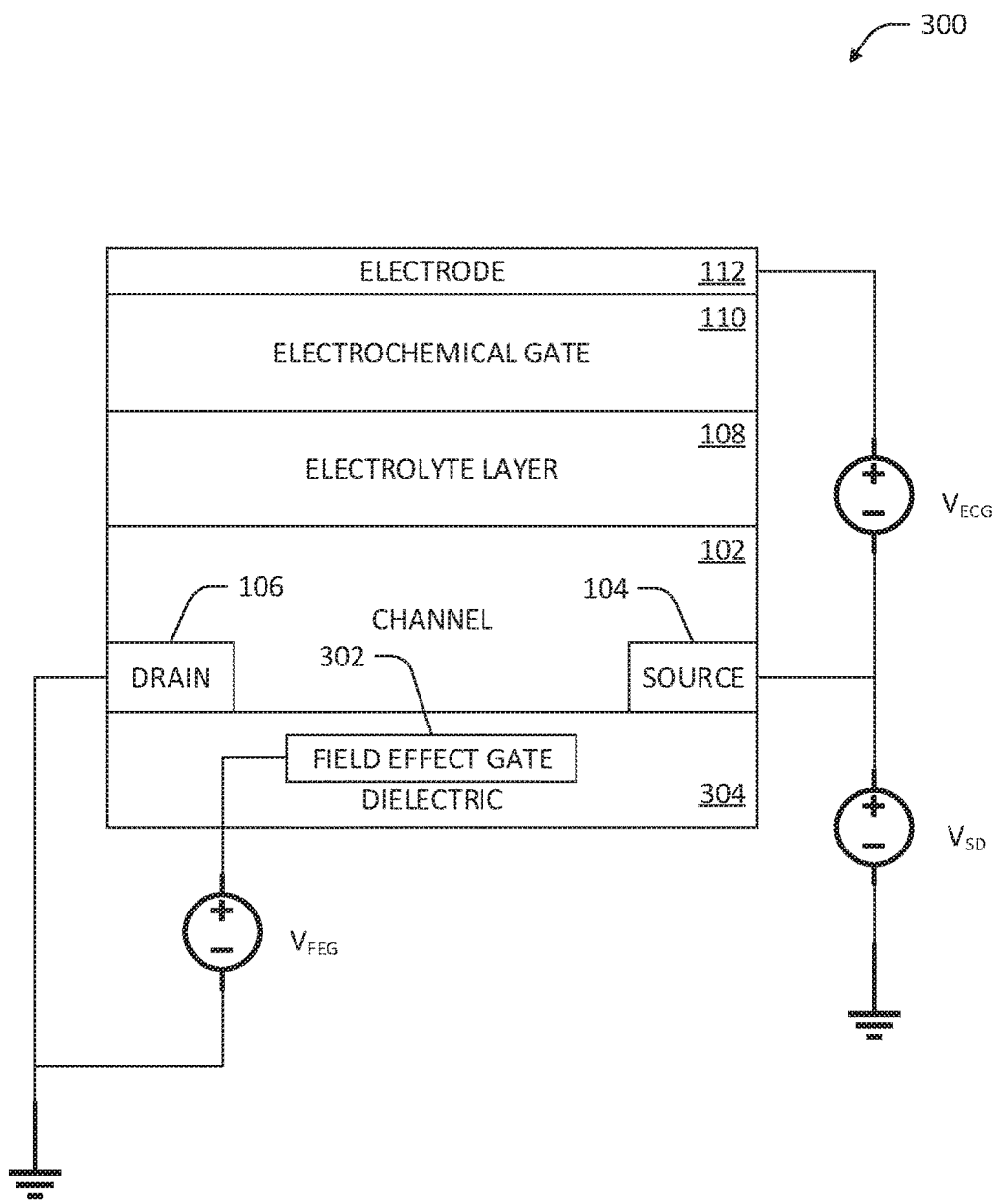
FIG. 3 is a block diagram of an exemplary ionic transistor usable as a field-effect transistor.

Referring now to FIG. 3, an exemplary ionic electronic transistor 300 that can be operated as a field-effect transistor (FET) is illustrated. The transistor 300 includes a field effect gate (FEG) 302 embedded in a dielectric substrate layer 304. The transistor 300 further includes the source 104 and drain 106, and the channel 102, which can be deposited on top of the dielectric substrate 304. The FEG 302 is physically and electrically isolated from the channel 102, source 104, and drain 106 by the dielectric 304. As in the transistor 100 described above with respect to FIG. 1, the electrolyte layer 108 is deposited on top of the channel layer 102 and the ECG layer 110 is deposited on a side of the electrolyte layer 108 opposite the side of the electrolyte layer 108 that makes contact with the channel layer 102, such that the ECG layer 110 is physically separated from the channel layer 102. The transistor 300 can further comprise the electrode 112, deposited on top of the ECG 110, and the voltage $V_{ECG}$ can be applied to the ECG 110 and the channel 102 by way of the electrode 112 and the source electrode 104.

As described above with respect to FIGS. 1 and 2, the conductance of the channel layer 102 can be changed in a non-volatile manner by application of voltage pulses at $V_{ECG}$. As in a conventional FET, when a voltage is applied to the FEG 302 at $V_{FEG}$, an electric field changes the conductance of the channel layer 102, and when the voltage is removed the electric field collapses and the conductance of the channel 102 returns to its value prior to application of the voltage at $V_{FEG}$. The transistor 300 therefore can function as a tunable FET. By application of voltage pulses at $V_{ECG}$, the conductance of the channel 102 can be tuned in a non-volatile manner, such that when the voltage at $V_{ECG}$ is removed the conductance of the channel 102 holds its value. By contrast, application of a voltage to the field effect gate 302 at $V_{FEG}$ changes the conductance of the channel 102 in a volatile manner, such that when the voltage at $V_{FEG}$ is removed the conductance of the channel 102 does not hold its value.

It is to be understood that the transistors 100 and 300 can be included in integrated circuits, where an integrated circuit can comprise one or both of the transistors 100 and 300 as well as other electronic components. It is further to be understood that voltages described herein as being applied to one or more parts of the transistors 100 and 300 can be applied by the other electronic components in the course of operation of such an integrated circuit.

From the foregoing, it can be understood that an ionic electronic transistor as described in detail above may be suitable for neuromorphic computing applications. In particular, the ionic electronic transistor is suited to applications wherein it is desirable that an input signal to a circuit affect a future output of the circuit. For example, the voltage $V_{ECG}$ can be considered an input to the transistors 100 and 300 and a current flowing between the source 104 and the drain 106 can be considered an output under a constant voltage $V_{SD}$. An input voltage pulse at $V_{ECG}$ changes the conductance of the channel, and thus changes the current flowing between the source 104 and the drain 106 when the voltage $V_{SD}$ stays constant. Since the conductance of the channel can be changed in a linear, reversible manner responsive to a series of voltage pulses at $V_{ECG}$, the output (source-drain current) of the transistors 100 and 300 can change predictably based upon prior inputs.

Figure 4:
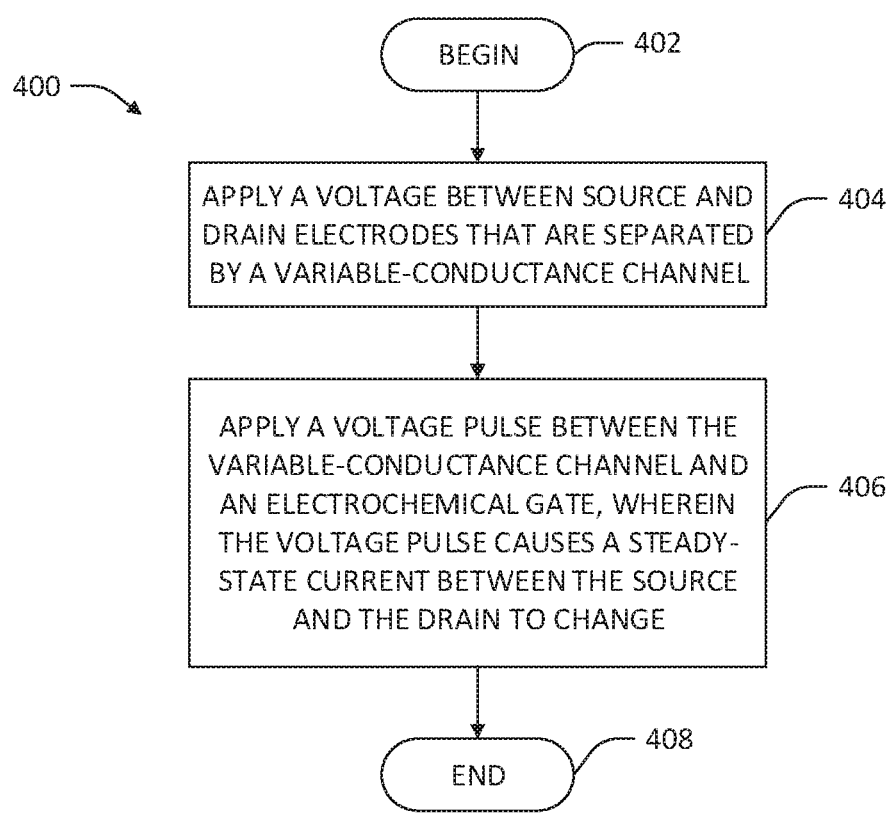
FIG. 4 is flow diagram that illustrates an exemplary methodology for operation of an ionic transistor.

FIG. 4 illustrates an exemplary methodology relating to operation of an ionic transistor. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Referring now to FIG. 4, a methodology 400 that facilitates operation of an ionic electronic transistor is illustrated. The methodology 400 begins at 402, and at 404 a voltage is applied between source and drain electrodes that are physically separated by a variable-conductance channel. The voltage causes a current to flow between the source and the drain electrodes through the variable-conductance channel, wherein the magnitude of the current is based upon a conductance of the channel. At 406 a voltage pulse is applied between the variable-conductance channel that separates the source and the drain electrodes and an ECG. The voltage pulse causes ions to migrate into the channel from the ECG or into the ECG from the channel, depending upon a polarity of the voltage pulse and a charge of the ions. The migration of the ions into or out of the channel causes a change in conductance of the channel from a first value prior to the voltage pulse to a second value after the voltage pulse. As the conductance of the channel changes from the first value to the second value responsive to application of the voltage pulse, the current flowing between the source and the drain changes from a first steady-state value to a second steady-state value (assuming that the voltage between the source and the drain electrodes is constant). The methodology 400 completes at 408.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A transistor device, comprising:
a variable-conductance channel layer;
a drain electrode in physical contact with the channel layer;
a source electrode in physical contact with the channel layer and physically separated from the drain electrode by the channel layer;
an electrolyte layer positioned on top of the channel layer; and
an electrochemical gate (ECG) layer positioned on top of the electrolyte layer, wherein the electrolyte layer physically separates the ECG layer and the channel layer, and wherein responsive to a voltage pulse being applied between the ECG layer and the channel layer, ions migrate from the ECG layer to the channel layer or from the channel layer to the ECG layer, and a conductance of the channel layer changes.

2. The transistor device of claim 1, wherein the variable-conductance channel layer comprises a lithium compound.

3. The transistor device of claim 2, wherein the lithium compound comprises lithium-cobalt-oxide ($LiCoO_2$).

4. The transistor device of claim 3, wherein the channel layer has a thickness of 1-120 nanometers.

5. The transistor device of claim 1, wherein the electrolyte layer comprises lithium phosphorous oxynitride (LiPON).

6. The transistor device of claim 5, wherein the electrolyte layer has a thickness of 20-400 nanometers.

7. The transistor device of claim 1, wherein the ECG layer comprises silicon.

8. The transistor device of claim 7, wherein the ECG layer has a thickness of 10-50 nanometers.

9. The transistor device of claim 1, wherein the channel layer and the ECG layer comprise a same material.

10. The transistor device of claim 9, wherein the electrolyte layer comprises a solid electrolyte.

* * * * *